United States Patent
Springer et al.

(10) Patent No.: US 11,699,215 B2
(45) Date of Patent: Jul. 11, 2023

(54) IMAGING DEVICE, METHOD AND PROGRAM FOR PRODUCING IMAGES OF A SCENE HAVING AN EXTENDED DEPTH OF FIELD WITH GOOD CONTRAST

(71) Applicant: Sony Corporation, Tokyo (JP)

(72) Inventors: Paul Springer, Stuttgart (DE); Zoltan Facius, Stuttgart (DE); Thimo Emmerich, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 709 days.

(21) Appl. No.: 16/642,382

(22) PCT Filed: Sep. 5, 2018

(86) PCT No.: PCT/EP2018/073889
§ 371 (c)(1),
(2) Date: Feb. 27, 2020

(87) PCT Pub. No.: WO2019/048492
PCT Pub. Date: Mar. 14, 2019

(65) Prior Publication Data
US 2020/0345215 A1 Nov. 5, 2020

(30) Foreign Application Priority Data
Sep. 8, 2017 (EP) .................................... 17190200

(51) Int. Cl.
*G06T 5/00* (2006.01)
*A61B 1/00* (2006.01)
(Continued)

(52) U.S. Cl.
CPC .......... *G06T 5/003* (2013.01); *A61B 1/00009* (2013.01); *A61B 1/000095* (2022.02);
(Continued)

(58) Field of Classification Search
None
See application file for complete search history.

(56) References Cited

U.S. PATENT DOCUMENTS 7,920,172 B2 * 4/2011 Chanas .............. H04N 5/35721
348/222.1
8,270,083 B2 * 9/2012 Liege ................. G02B 27/4211
359/618
(Continued)

FOREIGN PATENT DOCUMENTS

DE 102019208114 B4 * 3/2022 ........... G01B 11/005
GB 2486878 A * 7/2012 ......... H04N 13/0214
(Continued)

OTHER PUBLICATIONS

International Search Report and Written Opinion dated Oct. 19, 2018 for PCT/EP2018/073889 filed on Sep. 5, 2018, 10 pages.
(Continued)

*Primary Examiner* — John P Leubecker
(74) *Attorney, Agent, or Firm* — Xsensus LLP

(57) ABSTRACT

An imaging device for producing images of a scene, the imaging device comprising: a first and a second hyperchromatic lens being arranged in a stereoscopic configuration to receive light from the scene; image sensor circuitry configured to capture a first and second image of the light encountered by the first and the second lens respectively; processor circuitry configured to: produce depth information using the captured first and second images of the scene and produce a resultant first and second image of the scene using both the captured first and second image and the depth information.

15 Claims, 15 Drawing Sheets

(51) Int. Cl.
    *H04N 23/50* (2023.01)
    *H04N 23/56* (2023.01)
(52) U.S. Cl.
    CPC ...... *A61B 1/00186* (2013.01); *A61B 1/00193* (2013.01); *H04N 23/56* (2023.01); *H04N 23/555* (2023.01)

(56) References Cited

U.S. PATENT DOCUMENTS

| | | | |
|---|---|---|---|
| 2005/0020926 A1 | 1/2005 | Wiklof et al. | |
| 2010/0172020 A1* | 7/2010 | Price | G02B 21/244 359/383 |
| 2011/0286634 A1* | 11/2011 | Imamura | H04N 5/23232 382/106 |
| 2012/0200726 A1* | 8/2012 | Bugnariu | H04N 5/232125 348/222.1 |
| 2013/0215299 A1* | 8/2013 | Imamura | G02B 5/1885 348/272 |
| 2013/0278726 A1* | 10/2013 | Muhammad | H04N 9/04517 348/46 |
| 2017/0237960 A1* | 8/2017 | Kamm | H04N 5/2256 348/46 |
| 2017/0251911 A1* | 9/2017 | Ito | H04N 5/23296 |
| 2018/0011308 A1* | 1/2018 | Zhao | A61B 1/00188 |
| 2018/0075612 A1* | 3/2018 | Michielin | G06T 7/521 |
| 2019/0158803 A1* | 5/2019 | Mizukura | H04N 5/23264 |
| 2020/0104983 A1* | 4/2020 | Wang | A61B 1/041 |

FOREIGN PATENT DOCUMENTS

| | | | |
|---|---|---|---|
| WO | 2012/095322 A1 | 7/2012 | |
| WO | 2013/025530 A1 | 2/2013 | |
| WO | WO-2015059346 A1 * | 4/2015 | G01B 11/24 |
| WO | 2016/071020 A1 | 5/2016 | |
| WO | 2016/156149 A1 | 10/2016 | |

OTHER PUBLICATIONS

Wang, Y., et al., "3D endoscope system of monoscopic endoscope with external stereo lens", Retrieved from the Internet URL: https://www.sages.org/meetings/annual-meeting/abstracts-archive/3d-e . . . , on Dec. 21, 2016, 3 pages.

* cited by examiner

IMAGING DEVICE, METHOD AND PROGRAM FOR PRODUCING IMAGES OF A SCENE HAVING AN EXTENDED DEPTH OF FIELD WITH GOOD CONTRAST

CROSS-REFERENCE TO RELATED APPLICATIONS

The present application is based on PCT filing PCT/EP2018/073889, filed Sep. 5, 2018, which claims priority to EP 17190200.0, filed Sep. 8, 2017, the entire contents of each are incorporated herein by reference.

BACKGROUND

Field of the Disclosure

The present disclosure generally relates to an imaging device, method and program for producing images of a scene.

Description of the Related Art

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

Imaging devices are often limited in optical performance in many ways, due to the specific requirements and limitations peculiar to their application. A particular problem is the limited depth of field at which high spatial frequencies can be obtained in order to capture a sufficiently sharp image. In general, reducing the aperture size (which can also be described as an increase in aperture number) leads to an increase in the depth of field. However, reducing the aperture size leads to a reduction in the amount of light that can be collected at sensor level, resulting in noisy and low contrast images.

Moreover, since imaging devices (such as endoscopes) are typically required to have small form factors, maintaining a sufficiently high resolution image is generally achieved by reducing pixel sensor size. This in turn demands a low aperture number (or increase in physical aperture size) and a high effort on optical design to transfer higher spatial frequencies.

As such there is a trade off between high aperture number, resulting in images having a wide depth of field but with increased noise and poor contrast, and low aperture number, resulting in high resolution images with a narrow depth of field. Therefore a problem when performing imaging (such as when using a medical endoscope, a surgical microscope, or an industrial endoscopic device) is how to provide high resolution images while maintaining a wide depth of field. It is an aim of the present disclosure to address this issue.

SUMMARY

According to embodiments of the disclosure, there is an imaging device that comprises a first and a second hyperchromatic lens being arranged in a stereoscopic configuration to receive light from the scene, image sensor circuitry configured to capture a first and second image of the light encountered by the first and the second lens respectively, and processor circuitry configured to: produce depth information using the captured first and second images of the scene and produce a resultant first and second image of the scene using both the captured first and second image and the depth information.

According to embodiments of the disclosure, there is a method for producing images of a scene, the method comprising receiving light from a scene using a first and a second hyperchromatic lens arranged in a stereoscopic configuration; capturing a first and second image of the light encountered by the first and second lens respectively; producing depth information using the captured first and second images of the scene; and producing a resultant first and second image of the scene using both the first and second image and the depth information.

According to embodiments of the disclosure, there is a recording medium storing a computer program for controlling a computer to perform a method for producing images of a scene, the method comprising receiving light from a scene using a first and a second hyperchromatic lens arranged in a stereoscopic configuration; capturing a first and second image of the light encountered by the first and second lens respectively; producing depth information using the captured first and second images of the scene; and producing a resultant first and second image of the scene using both the first and second image and the depth information.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1:
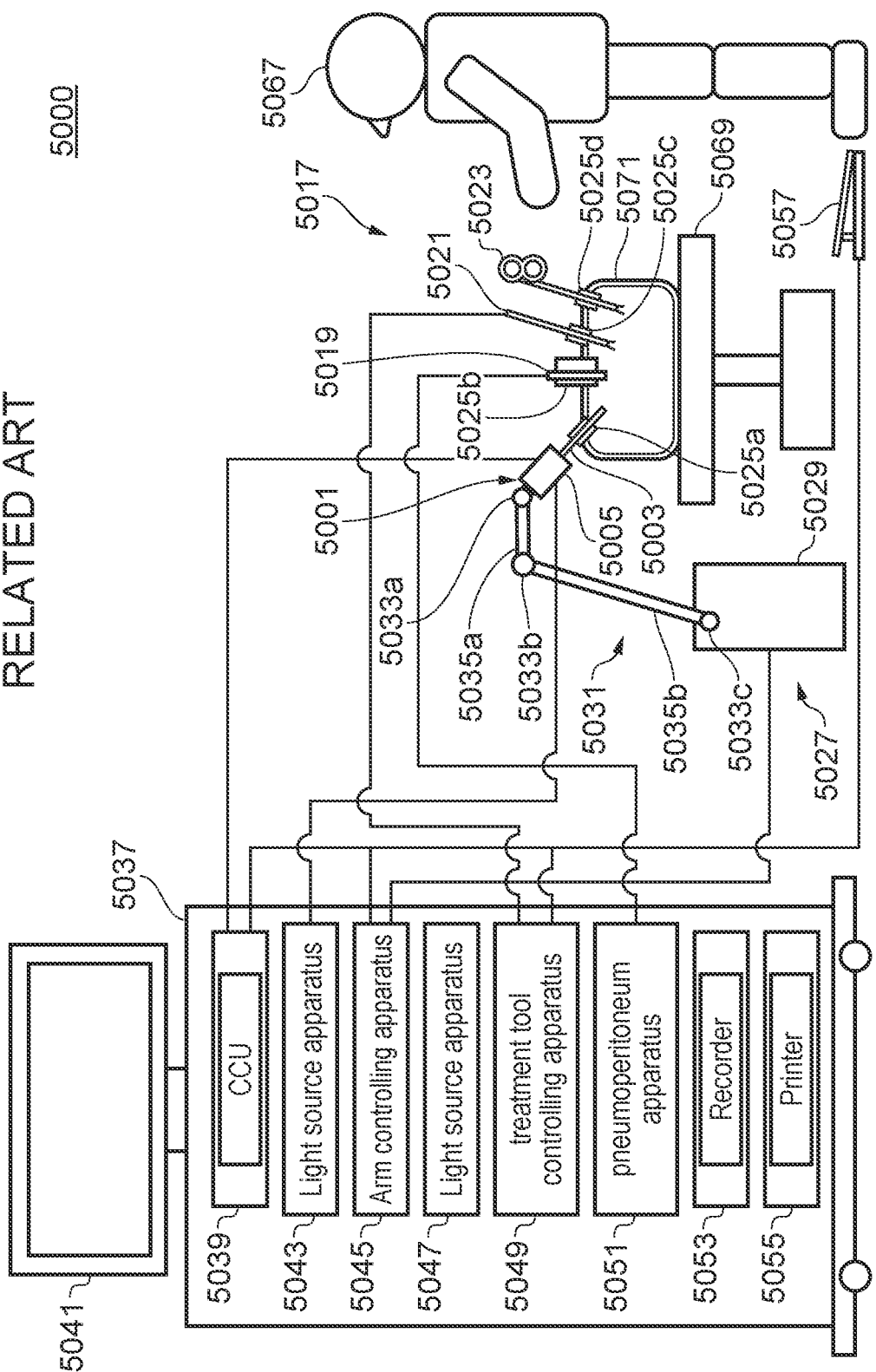
FIG. 1 is a view depicting an example of a schematic configuration of an endoscopic surgery system to which the technology according to an embodiment of the present disclosure can be applied.

Referring now to the drawings, wherein like reference numerals designate identical or corresponding parts throughout the several views.

Application

<<Application>>

The technology according to an embodiment of the present disclosure can be applied to various products. For example, the technology according to an embodiment of the present disclosure may be applied to an endoscopic surgery system, surgical microscopy or medical imaging device or other kind of industrial endoscopy in, say pipe or tube laying or fault finding.

FIG. 1 is a view depicting an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069. As depicted, the endoscopic surgery system 5000 includes an endoscope 5001, other surgical tools 5017, a supporting arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d are used to puncture the abdominal wall. Then, a lens barrel 5003 of the endoscope 5001 and the other surgical tools 5017 are inserted into body lumens of the patient 5071 through the trocars 5025a to 5025d. In the example depicted, as the other surgical tools 5017, a pneumoperitoneum tube 5019, an energy treatment tool 5021 and forceps 5023 are inserted into body lumens of the patient 5071. Further, the energy treatment tool 5021 is a treatment tool for performing incision and peeling of a tissue, sealing of a blood vessel or the like by high frequency current or ultrasonic vibration. However, the surgical tools 5017 depicted are mere examples at all, and as the surgical tools 5017, various surgical tools which are generally used in endoscopic surgery such as, for example, a pair of tweezers or a retractor may be used.

An image of a surgical region in a body lumen of the patient 5071 imaged by the endoscope 5001 is displayed on a display apparatus 5041. The surgeon 5067 would use the energy treatment tool 5021 or the forceps 5023 while watching the image of the surgical region displayed on the display apparatus 5041 on the real time basis to perform such treatment as, for example, resection of an affected area. It is to be noted that, though not depicted, the pneumoperitoneum tube 5019, the energy treatment tool 5021 and the forceps 5023 are supported by the surgeon 5067, an assistant or the like during surgery.

(Supporting Arm Apparatus)

The supporting arm apparatus 5027 includes an arm unit 5031 extending from a base unit 5029. In the example depicted, the arm unit 5031 includes joint portions 5033a, 5033b and 5033c and links 5035a and 5035b and is driven under the control of an arm controlling apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body lumen of the patient 5071, and a camera head 5005 connected to a proximal end of the lens barrel 5003. In the example depicted, the endoscope 5001 is depicted which includes as a hard mirror having the lens barrel 5003 of the hard type. However, the endoscope 5001 may otherwise be configured as a soft mirror having the lens barrel 5003 of the soft type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body lumen of the patient 5071 through the objective lens. It is to be noted that the endoscope 5001 may be a direct view mirror or may be a perspective view mirror or a side view mirror.

An optical system and an image pickup element are provided in the inside of the camera head 5005 such that reflected light (observation light) from an observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display), a plurality of image pickup elements may be provided on the camera head 5005. In this case, a plurality of relay optical systems are provided in the inside of the lens barrel 5003 in order to guide observation light to each of the plurality of image pickup elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an image pickup condition such as a magnification or a focal distance.

The display apparatus 5041 displays an image based on an image signal for which the image processes have been performed by the CCU 5039 under the control of the CCU 5039. If the endoscope 5001 is ready for imaging of a high resolution such as 4K (horizontal pixel number 3840× vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of equal to or not less than 55 inches, then a more immersive experience can be obtained. Further, a plurality of display apparatus 5041 having different resolutions and/or different sizes may be provided in accordance with purposes.

The light source apparatus 5043 includes a light source such as, for example, a light emitting diode (LED) and supplies irradiation light for imaging of a surgical region to the endoscope 5001.

The arm controlling apparatus 5045 includes a processor such as, for example, a CPU and operates in accordance with a predetermined program to control driving of the arm unit 5031 of the supporting arm apparatus 5027 in accordance with a predetermined controlling method.

An inputting apparatus 5047 is an input interface for the endoscopic surgery system 5000. A user can perform inputting of various kinds of information or instruction inputting to the endoscopic surgery system 5000 through the inputting apparatus 5047. For example, the user would input various kinds of information relating to surgery such as physical information of a patient, information regarding a surgical procedure of the surgery and so forth through the inputting apparatus 5047. Further, the user would input, for example, an instruction to drive the arm unit 5031, an instruction to change an image pickup condition (type of irradiation light, magnification, focal distance or the like) by the endoscope 5001, an instruction to drive the energy treatment tool 5021 or the like through the inputting apparatus 5047.

The type of the inputting apparatus 5047 is not limited and may be that of any one of various known inputting apparatus. As the inputting apparatus 5047, for example, a mouse, a keyboard, a touch panel, a switch, a foot switch 5057 and/or a lever or the like may be applied. Where a touch panel is used as the inputting apparatus 5047, it may be provided on the display face of the display apparatus 5041.

Otherwise, the inputting apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the inputting apparatus 5047 includes a camera which can detect a motion of a user, and various kinds of inputting are performed in response to a gesture or a line of sight of a user detected from a video imaged by the camera. Further, the inputting apparatus 5047 includes a microphone which can collect the voice of a user, and various kinds of inputting are performed by voice collected by the microphone. By configuring the inputting apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, the convenience to the user is improved.

A treatment tool controlling apparatus 5049 controls driving of the energy treatment tool 5021 for cautery or incision of a tissue, sealing of a blood vessel or the like. A pneumoperitoneum apparatus 5051 feeds gas into a body lumen of the patient 5071 through the pneumoperitoneum tube 5019 to inflate the body lumen in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Supporting Arm Apparatus)

The supporting arm apparatus 5027 includes the base unit 5029 serving as a base, and the arm unit 5031 extending from the base unit 5029. In the example depicted, the arm unit 5031 includes the plurality of joint portions 5033*a*, 5033*b* and 5033*c* and the plurality of links 5035*a* and 5035*b* connected to each other by the joint portion 5033*b*. In FIG. 1, for simplified illustration, the configuration of the arm unit 5031 is depicted in a simplified form. Actually, the shape, number and arrangement of the joint portions 5033*a* to 5033*c* and the links 5035*a* and 5035*b* and the direction and so forth of axes of rotation of the joint portions 5033*a* to 5033*c* can be set suitably such that the arm unit 5031 has a desired degree of freedom. For example, the arm unit 5031 may preferably be configured such that it has a degree of freedom equal to or not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body lumen of the patient 5071.

An actuator is provided in each of the joint portions 5033*a* to 5033*c*, and the joint portions 5033*a* to 5033*c* are configured such that they are rotatable around predetermined axes of rotation thereof by driving of the respective actuators. The driving of the actuators is controlled by the arm controlling apparatus 5045 to control the rotational angle of each of the joint portions 5033*a* to 5033*c* thereby to control driving of the arm unit 5031. Consequently, control of the position and the posture of the endoscope 5001 can be implemented.

Thereupon, the arm controlling apparatus 5045 can control driving of the arm unit 5031 by various known controlling methods such as force control or position control.

For example, if the surgeon 5067 suitably performs operation inputting through the inputting apparatus 5047 (including the foot switch 5057), then driving of the arm unit 5031 may be controlled suitably by the arm controlling apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the inputting apparatus 5047 which is placed at a place remote from the surgery room.

Further, where force control is applied, the arm controlling apparatus 5045 may perform power-assisted control to drive the actuators of the joint portions 5033a to 5033c such that the arm unit 5031 may receive external force by the user and move smoothly following the external force. This makes it possible to move, when the user directly touches with and moves the arm unit 5031, the arm unit 5031 with comparatively weak force. Accordingly, it becomes possible for the user to move the endoscope 5001 more intuitively by a simpler and easier operation, and the convenience to the user can be improved.

Here, generally in endoscopic surgery, the endoscope 5001 is supported by a medical doctor called scopist. In contrast, where the supporting arm apparatus 5027 is used, the position of the endoscope 5001 can be fixed more certainly without hands, and therefore, an image of a surgical region can be obtained stably and surgery can be performed smoothly.

It is to be noted that the arm controlling apparatus 5045 may not necessarily be provided on the cart 5037. Further, the arm controlling apparatus 5045 may not necessarily be a single apparatus. For example, the arm controlling apparatus 5045 may be provided in each of the joint portions 5033a to 5033c of the arm unit 5031 of the supporting arm apparatus 5027 such that the plurality of arm controlling apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each colour (each wavelength), adjustment of the white balance of a picked up image can be performed by the light source apparatus 5043. Further, in this case, if laser beams from the respective RGB laser light sources are irradiated time-divisionally on an observation target and driving of the image pickup elements of the camera head 5005 is controlled in synchronism with the irradiation timings, then images individually corresponding to the R, G and B colours can be picked up time-divisionally. According to the method just described, a colour image can be obtained even if a colour filter is not provided for the image pickup element.

Further, driving of the light source apparatus 5043 may be controlled such that the intensity of light to be outputted is changed for each predetermined time. By controlling driving of the image pickup element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. This may include, but not be limited to laser light such as that provided by a Vertical Cavity surface laser or any kind of laser light. Alternatively or additionally, the light may be InfraRed (IR) light. In special light observation, for example, by utilizing the wavelength dependency of absorption of light in a body tissue to irradiate light of a narrower band in comparison with irradiation light upon ordinary observation (namely, white light), narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 5043 can be configured to supply such narrowband light and/or excitation light suitable for special light observation as described above. The light source may also apply a heat pattern to an area. This heat pattern will be explained later with reference to FIGS. 3A-C. The light source apparatus 5043 is, in embodiments, a Vertical Cavity Surface-Emitting Laser (VCSEL) which can produce light in the visible part of the electromagnetic spectrum and some produce light in the Infra-Red part of the electromagnetic spectrum. In this respect, the light source apparatus 5043 may also act as a visible light source illuminating the area. The light source apparatus 5043 is, in embodiments, one or more Vertical Cavity Surface-Emitting Laser (VCSEL) which can produce light in the visible part of the electromagnetic spectrum and some produce light in the Infra-Red part of the electromagnetic spectrum. In this respect, the light source apparatus 5043 may also act as a visible light source illuminating the area. The one or more VCSELs may be single wavelength narrowband VCSELs, where each VCSEL varies in emission spectral frequency. Alternatively, or additionally, one or more of the VCSELs may be a Micro Electro Mechanical system (MEMs) type VCSEL whose wavelength emission may be altered over a specific range. In embodiments of the disclosure, the wavelength may alter over the range 550 nm to 650 nm or 600 nm to 650 nm. The shape of the VCSEL may vary such as a square or circular shape and may be positioned at one or varying positions in the endoscope 5001.

The light source apparatus 5043 may illuminate one or more areas. This may be achieved by selectively switching the VCSELs on or by performing a raster scan of the area using a Micro Electro Mechanical system (MEMs). The purpose of the light source apparatus 5043 is to perform Spatial Light Modulation (SLM) on the light over the area. This will be explained in more detail later.

It should be noted that although the foregoing describes the light source apparatus 5043 as being positioned in the cart, the disclosure is not so limited. In particular, the light source apparatus may be positioned in the camera head 5005.

(Camera Head and CCU)

Figure 2:
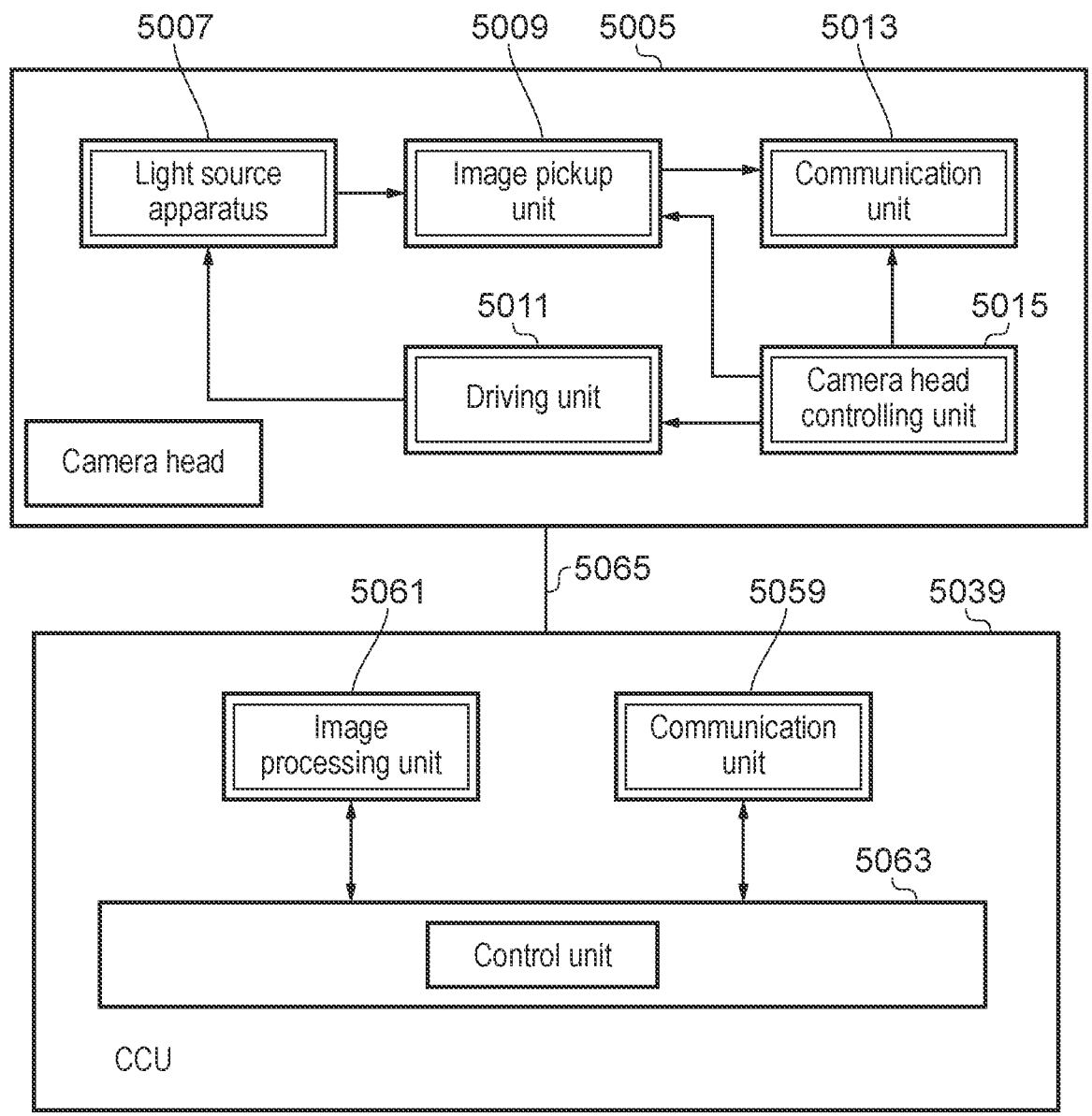
FIG. 2 is a block diagram depicting an example of a functional configuration of the camera head and the CCU depicted in FIG. 1.

Functions of the camera head 5005 of the endoscope 5001 and the CCU 5039 are described in more detail with reference to FIG. 2. FIG. 2 is a block diagram depicting an example of a functional configuration of the camera head 5005 and the CCU 5039 depicted in FIG. 1.

Referring to FIG. 2, the camera head 5005 has, as functions thereof, a lens unit 5007, an image pickup unit 5009, a driving unit 5011, a communication unit 5013 and a camera head controlling unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the image pickup element of the image pickup unit 5009. Further, the zoom lens and the focusing lens are configured such that the positions thereof on their optical axis are movable for adjustment of the magnification and the focal point of a picked up image.

The image pickup unit 5009 includes an image pickup element and disposed at a succeeding stage to the lens unit 5007. Observation light having passed through the lens unit 5007 is condensed on the light receiving face of the image pickup element, and an image signal corresponding to the observation image is generated by photoelectric conversion of the image pickup element. The image signal generated by the image pickup unit 5009 is provided to the communication unit 5013.

As the image pickup element which is included by the image pickup unit 5009, an image sensor, for example, of the complementary metal oxide semiconductor (CMOS) type is used which has a Bayer array and is capable of picking up an image in colour. It is to be noted that, as the image pickup element, an image pickup element may be used which is ready, for example, for imaging of an image of a high resolution equal to or not less than 4K. If an image of a surgical region is obtained in a high resolution, then the surgeon 5067 can comprehend a state of the surgical region in enhanced details and can proceed with the surgery more smoothly.

Further, the image pickup element which is included by the image pickup unit 5009 includes such that it has a pair of image pickup elements for acquiring image signals for the right eye and the left eye compatible with 3D display. Where 3D display is applied, the surgeon 5067 can comprehend the depth of a living body tissue in the surgical region more accurately. It is to be noted that, if the image pickup unit 5009 is configured as that of the multi-plate type, then a plurality of systems of lens units 5007 are provided corresponding to the individual image pickup elements of the image pickup unit 5009.

The image pickup unit 5009 may not necessarily be provided on the camera head 5005. For example, the image pickup unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head controlling unit 5015. Consequently, the magnification and the focal point of a picked up image by the image pickup unit 5009 can be adjusted suitably.

The communication unit 5013 includes a communication apparatus for transmitting and receiving various kinds of information to and from the CCU 5039. The communication unit 5013 transmits an image signal acquired from the image pickup unit 5009 as RAW data to the CCU 5039 through the transmission cable 5065. Thereupon, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to image pickup conditions such as, for example, information that a frame rate of a picked up image is designated, information that an exposure value upon image picking up is designated and/or information that a magnification and a focal point of a picked up image are designated.

The communication unit 5013 provides the received control signal to the camera head controlling unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head controlling unit 5015.

It is to be noted that the image pickup conditions such as the frame rate, exposure value, magnification or focal point are set automatically by the control unit 5063 of the CCU 5039 on the basis of an acquired image signal. In other words, an auto exposure (AE) function, an auto focus (AF) function and an auto white balance (AWB) function are incorporated in the endoscope 5001.

The camera head controlling unit 5015 controls driving of the camera head 5005 on the basis of a control signal from the CCU 5039 received through the communication unit 5013. For example, the camera head controlling unit 5015 controls driving of the image pickup element of the image pickup unit 5009 on the basis of information that a frame rate of a picked up image is designated and/or information that an exposure value upon image picking up is designated. Further, for example, the camera head controlling unit 5015 controls the driving unit 5011 to suitably move the zoom lens and the focus lens of the lens unit 5007 on the basis of information that a magnification and a focal point of a picked up image are designated. The camera head controlling unit 5015 may further include a function for storing information for identifying the lens barrel 5003 and/or the camera head 5005.

It is to be noted that, by disposing the components such as the lens unit 5007 and the image pickup unit 5009 in a sealed structure having high airtightness and waterproof, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. Thereupon, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process and/or an image stabilization process) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. Thereupon, if image pickup conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. Thereupon, the control unit 5063 recognizes various objects in the surgical region image using various image recognition technologies. For example, the control unit 5063 can recognize a surgical tool such as forceps, a particular living body region, bleeding, mist when the energy treatment tool 5021 is used and so forth by detecting the shape, colour and so forth of edges of the objects included in the surgical region image. The control unit 5063 causes, when it controls the display unit 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed with the surgery more safety and certainty.

The transmission cable 5065 which connects the camera head 5005 and the CCU 5039 to each other is an electric signal cable ready for communication of an electric signal, an optical fibre ready for optical communication or a composite cable ready for both of electrical and optical communication.

Here, while, in the example depicted, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the surgery room. Therefore, such a situation that movement of medical staff in the surgery room is disturbed by the transmission cable 5065 can be eliminated.

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a soft endoscopic system for inspection or a microscopic surgery system. Indeed, the technology may be applied to a surgical microscope for conducting neurosurgery or the like. Moreover, as would be apparent to the skilled person from at least the above examples, the technology may be applied more generally to any kind of medical imaging device.

The technology according to an embodiment of the present disclosure can be applied suitably to the CCU 5039 from among the components described hereinabove. Specifically, the technology according to an embodiment of the present disclosure is applied to an endoscopy system, surgical microscopy or medical imaging. By applying the technology according to an embodiment of the present disclosure to these areas, blood flow in veins, arteries and capillaries may be identified. Further, objects may be identified and the material of those objects may be established. This reduces the risk to the patient's safety during operations.

Figure 3A:
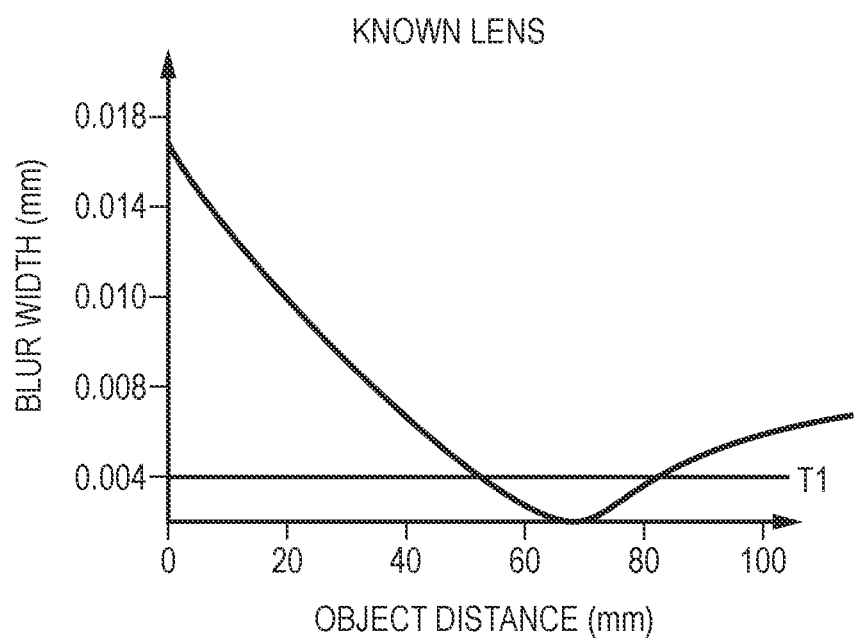
FIGS. 3A and 3B depict the depth of field of an image formed by a known lens.
Figure 3B:
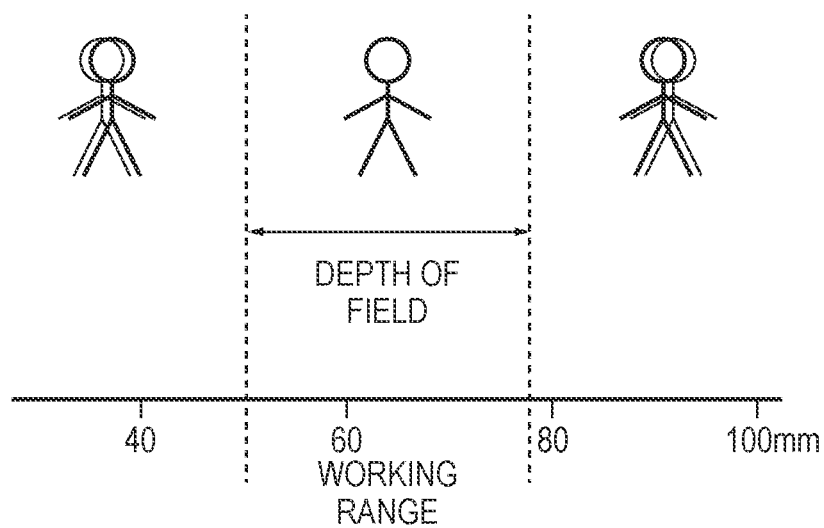

FIGS. 3A and 3B depict the depth of field of an image formed by a known lens. In FIG. 3A the blur width is an indication of the level of sharpness or focus within an image. Threshold T1 indicates an acceptable level of blur width in the image. That is, while the blur width remains below the threshold level, there is an acceptable level of blur in the image and the image is in focus. For a known lens, there is an object distance corresponding to the focal length of the lens whereby the image of the object shall be in focus. The range of object distances whereby the blur width is below the threshold value T1 provides an indication of the effective depth of field of the image. As shown in FIG. 3B, the working range of the object distance relates to the depth of field of the image. If the object distance changes such that it is below (near field) or above (far field) the working range of the lens, then the image of the object shall move out of focus. That is, the blur width will increase above the threshold value T1.

Figure 4:
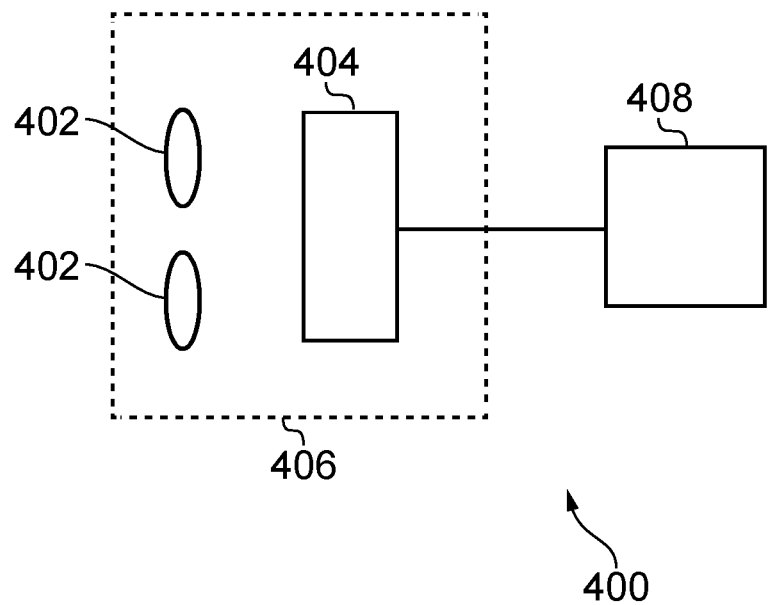
FIG. 4 is a schematic depiction of a medical imaging device 400 according to an embodiment of the disclosure such as can be employed in the surgery system of FIG. 1.

FIG. 4 is a schematic depiction of a medical imaging device 400 according to an embodiment of the disclosure such as can be employed in the surgery system of FIG. 1. The medical imaging device 400 comprises a first and a second hyperchromatic lens 402 arranged in a stereoscopic configuration. The medical imaging device 400 further comprises image sensor circuitry 404. Together, the first and second hyperchromatic lenses 402 and the image sensor circuitry 404 form the optical portion 406 of the medical imaging device 400. The medical imaging device 400 further comprises processor circuitry 408 connected to the optical portion 406 via image sensor circuitry 404. The optical portion 406 may be connected to the processor circuitry 408 using a wired connection as depicted in FIG. 4, or may alternatively be connected via a wireless link.

In operation, each of the first and second hyperchromatic lenses 402 receives light from a scene and forms an image of the scene on the image sensor circuitry 404. The image sensor circuitry 404 then captures a first and a second image of the light encountered by the first and the second hyperchromatic lens 402 respectively. Since the first and the second hyperchromatic lens 402 are arranged in a stereoscopic configuration the image sensor circuitry 404 is able to capture a first and a second image of the scene wherein the first and second image are images of the scene having a different view point. That is the first and second image of the scene view the scene from a different angle with respect to each other.

In the present embodiment, light from the scene used to form the captured image is received from a medical instrument such as that depicted in FIGS. 1 and 2. That is, the first and second hyperchromatic lens 402 receive light from the scene captured by the medical instrument and form the first and second image on the image sensor circuitry 404. It will be understood that light from the scene may be received from any other type of instrument, provided the light is encountered and focused by the first and second hyperchromatic lens 402 arranged in a stereoscopic configuration onto the image sensor circuitry 404.

Figure 5:
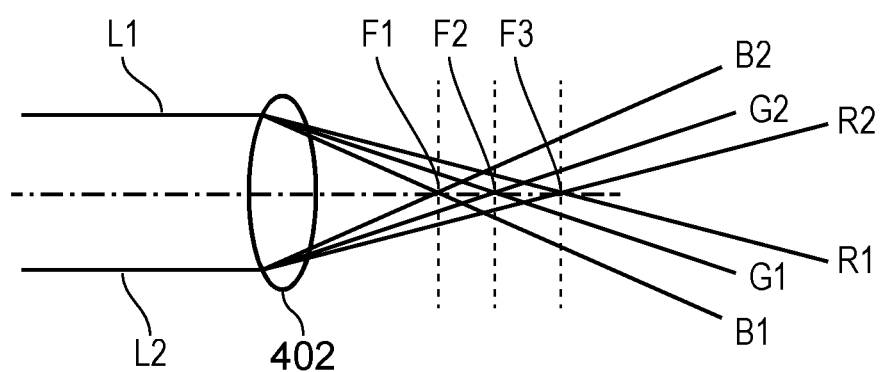
FIG. 5 is a depiction of light encountered by a single hyperchromatic lens 402 such as contained within the medical imaging device 400 of FIG. 4.

FIG. 5 is a depiction of light encountered by a single hyperchromatic lens 402 such as contained within the medical imaging device 400 of FIG. 4. The hyperchromatic lens 402 receives light rays L1 and L2 from a scene. Light rays L1 and L2 may be broadband light comprising light of a plurality of wavelengths. By virtue of the optical properties of the hyperchromatic lens 402, light of different wavelength is brought to a focus at a different distance from the hyperchromatic lens. That is, the hyperchromatic lens has a different focal point for light of different wavelength and different wavelengths of light are dispersed as they encounter the hyperchromatic lens 402. For example in FIG. 5 the hyperchromatic lens 402 is displaying axial chromatic aberration such that the different wavelengths of light contained in L1 and L2 have different focal points. The hyperchromatic lens may display other forms of chromatic aberration, such as longitudinal chromatic aberration (or magnification change), and this may be removed or accounted for in the medical imaging device as required by any appropriate technique. For example, longitudinal chromatic aberration may also be compensated for by the design of hyperchromatic lenses 402. For the example shown in FIG. 5, light beams L1 and L2 contain light of red (R), green (G) and blue (B) wavelengths. By virtue of the hyperchromatic properties of the lens the blue light, having the shorter wavelength, is brought to a focus at focal point F1, while red light of a longer wavelength is brought to a focus at focal point F3 which is located further from the hyperchromatic lens 402.

Figure 6:
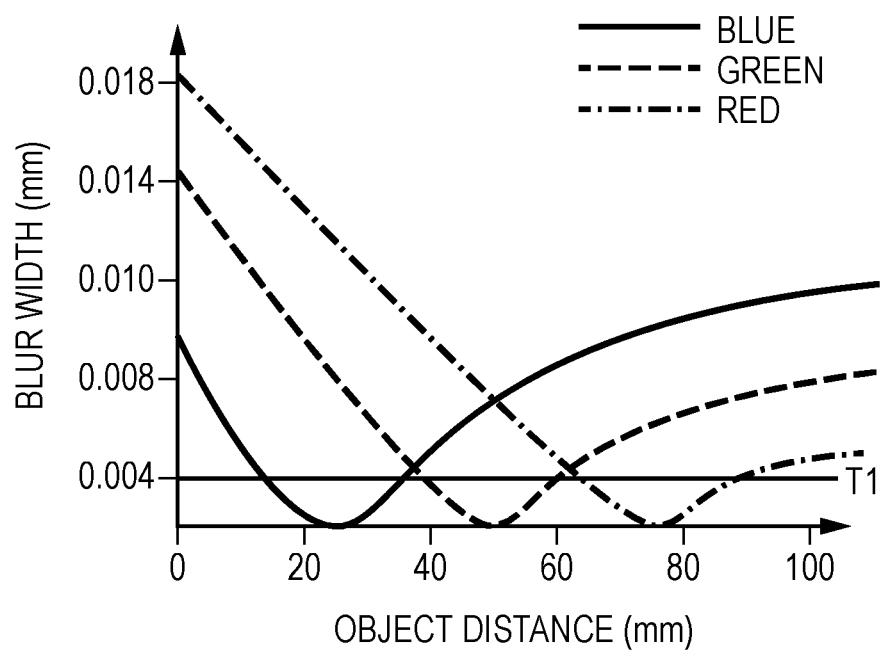
FIG. 6 shows a resultant graph of the blur width against wavelength for the optical portion 406 of the medical imaging device 400 of FIG. 4.

FIG. 6 shows a resultant graph of the blur width against wavelength for the optical portion 406 of the medical imaging device 400 of FIG. 4. Here, blur width is an indication of the level of focus or sharpness in an image. While the blur width remains under the threshold value T1, it may be considered that there is an acceptable level of sharpness in the image. The absolute value of the threshold T1 can be set according to the context of the application. Furthermore, it will be appreciated that any method of quantifying the level of blur within the image as known in the art may be used as appropriate. The width of the object distance where the blur width remains under the threshold value T1 gives an indication of the effective depth of field of the image. Since the light of different wavelengths is brought to a focus at different distance from the hyperchromatic lens there are three effective regions where the blur width is below the operational threshold, one for each of the wavelengths red, green and blue contained in the light beams L1 and L2 encountered by the hyperchromatic lenses 402. It will be understood by the skilled person that while three distinct wavelengths of light are depicted in FIGS. 5 and 6 various wavelengths of light may be contained in light beams L1 and L2. Furthermore, since the hyperchromatic lens 402 may focus light as a function of wavelength there may be any number of object distances at which light of a given wavelength is below the operational blur width threshold. Thus, for each wavelength of light a sharp image at a designed object distance may be acquired. As such low blur values are achievable over the working distance in at least one of the colour channels.

Returning to FIG. 4, the image sensor circuitry 404 may comprise a single sensor board or be formed from individual sensors for the first and second hyperchromatic lens 402. In some embodiments of the disclosure the image sensor circuitry may comprise a high resolution sensor, such as a 4K image sensor, 8K sensor or the like. The image sensor circuitry 404 is operable to capture the first and second image of the light from the scene received by the first and second hyperchromatic lens 402 as separate electronic images. Furthermore the image sensor circuitry 404 is operable to capture light of different wavelengths as separate colour channels in the electronic images. The image sensor may capture individual images or consecutive frames as in a video.

Figure 7:
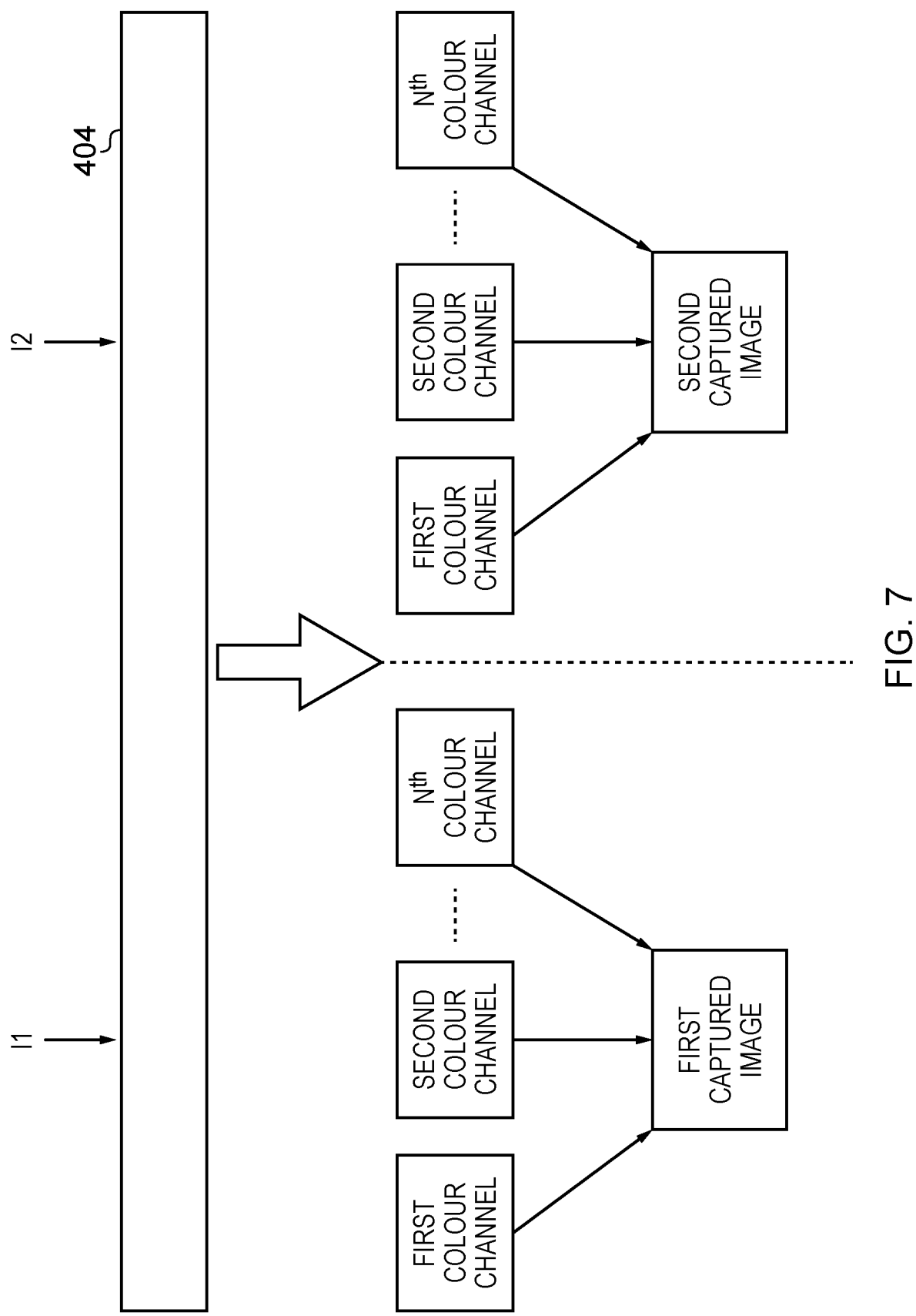
FIG. 7 demonstrates the detection of the first and second image by image sensor circuitry located in the medical imaging device according to an embodiment of the disclosure.
Figure 8:
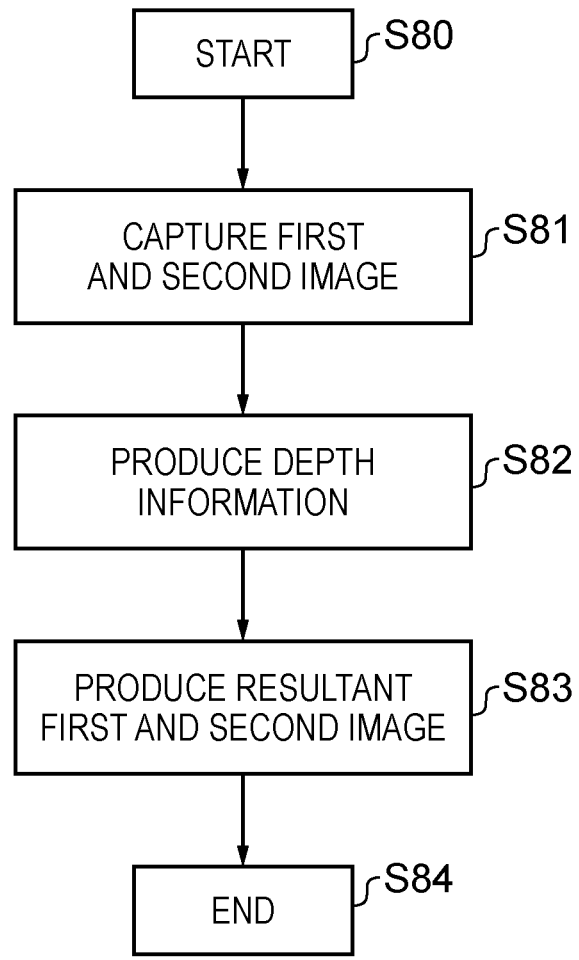
FIG. 8 is a flow chart depicting the processing steps performed by the image sensor circuitry and the processor circuitry according to an embodiment of the disclosure.

FIG. 7 demonstrates the detection of the first and second image by image sensor circuitry located in the medical imaging device according to an embodiment of the disclosure. The image sensor circuitry 404 receives images I1 and I2 focused by the first and second hyperchromatic lenses 402 respectively. It will be appreciated that I1 and I2 may comprise light of a plurality of wavelengths. Having been encountered by hyperchromatic lenses 402 as described above, the skilled person will understand that different wavelengths of light contained in I1 and I2 shall be chromatically separated such that they are at different levels of focus when encountered by image sensor circuitry 404. The image sensor circuitry 404 is operable to capture the light I1 and I2 as a separate first and second captured image respectively. Furthermore, as shown in FIG. 8, the image sensor circuitry is operable to detect a first plurality of colour channels for the first and second captured images. According to an embodiment of the disclosure the plurality of colour channels can be selected from, but are not limited to, infrared, red, green, blue and ultraviolet wavelengths.

Returning again to the operation of the medical imaging device 400 of FIG. 4, once the image sensor circuitry 404 has captured the first and second image of the scene, processor circuitry 408 receives the first and second image from the image sensor circuitry 404. The processor circuitry 408 then produces depth information of the scene using the stereoscopic properties of the first and second image of the scene. It will be appreciated that any suitable algorithm known in the art may be employed to produce the depth information of the scene using the first and second images. For example, since the first and second image of the scene are images of the scene captured at different viewpoints, the image processor circuitry may use binocular parallax information from the first and second image to triangulate the distance to an object or region of the scene and hence produce depth information of the scene.

After the image processor circuitry 408 has produced the depth information of the scene it is further configured to produce resultant first and second images of the scene using the first and second image of the scene captured by the image sensor circuitry 404 and the depth information.

FIG. 8 is a flow chart depicting the processing steps performed by the image sensor circuitry and the processor circuitry according to an embodiment of the disclosure. All algorithms performed by the image sensor circuitry 404 and the processor circuitry 408 may be developed to run in real time. Step S81 is performed by the image sensor circuitry 404 while steps S82 and S83 are performed by the processor circuitry 408. Processing begins at step S80 and progresses to step S81. The image sensor circuitry 404 then captures the first and second image of the scene in step S81 and transmits this information to the processor circuitry 408. The processor circuitry then produces depth information in step S82 using the stereoscopic properties of the first and second images of the scene captured by the image sensor circuitry 404. In step S83 the processor circuitry 408 produces a resultant first and second image of the scene using the first and second image of the scene captured by the image sensor circuitry 404 in step S81 and the depth information of the scene produced in step S82 by the processor circuitry 408. The processing ends in step S84.

The resultant images achieved according to embodiments of the disclosure may as such have extended depth of field over the complete working range of the medical imaging device 400. Consequentially, aperture number can be reduced to increase the sensitivity of the device without compromising the depth of field. According to embodiments of the disclosure the medical imaging device 400 is operable to produce high resolution resultant first and second images of the scene having an extended depth of field. The resultant first and second images of the scene may either be displayed as separate first and second images of the scene, or may be combined to produce a single 3D image of the scene having extended depth of field and may be stored and or displayed in real time.

Figure 9:
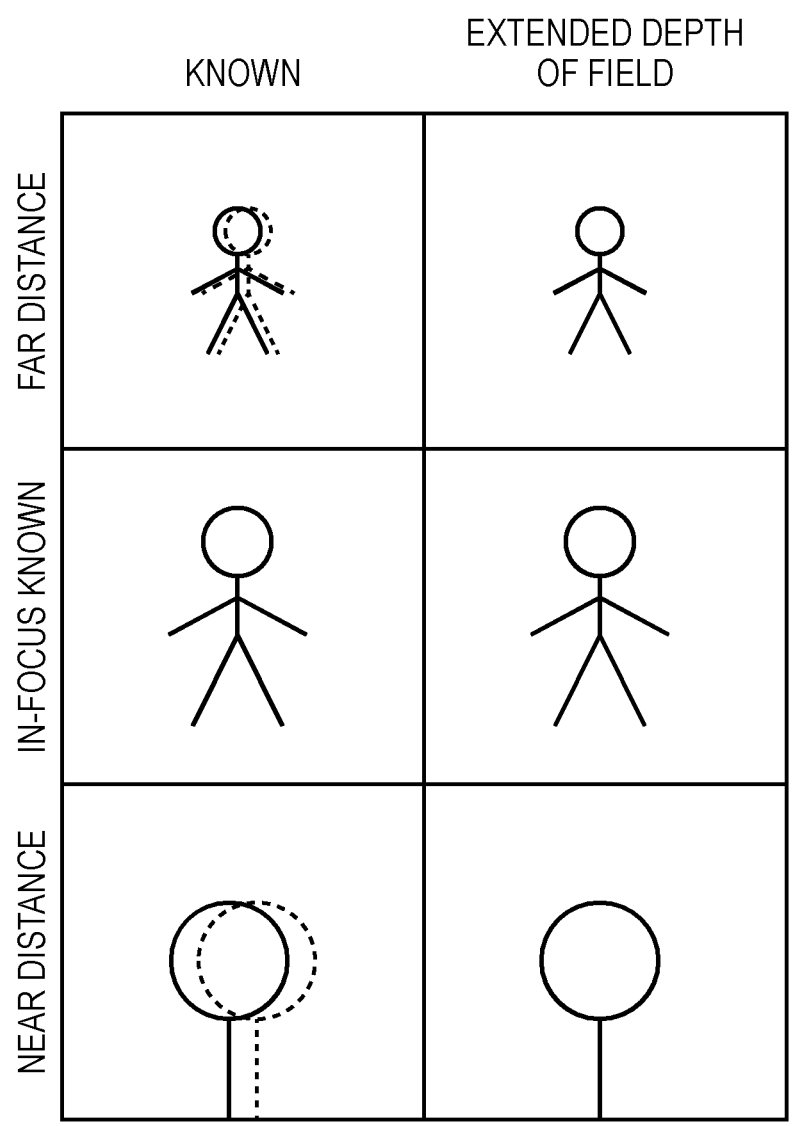
FIG. 9 is a depiction of images having extended depth of field produced using the medical imaging device of embodiments of the disclosure.

FIG. 9 is a depiction of images having extended depth of field produced using the medical imaging device of embodiments of the disclosure. In the case using a known lens, there is a single distance where the image captured by the imaging device is in focus, since the lens has a single focal length as demonstrated in FIG. 3B. Using the first and second hyperchromatic lens arranged in a stereoscopic configuration with the tailored digital image processing of embodiments of the disclosure it is possible to obtain images having an extended depth of field, such that images in the near and far field have increased sharpness levels without compromising the resolution of the images.

According to embodiments of the disclosure, hyperchromatic lenses with a focal length of 2 mm and an aperture number of F #=3 may be employed to effect. For example, a specific configuration of hyperchromatic lenses with a focal length of 2.08 mm and an aperture number of F #=2.78 may be used. Given such optical parameters, the medical imaging device according to embodiments of the disclosure may, for a circle of confusion (blur diameter) of 8 pixels, achieve an extended depth of field over a range of object distances of approximately 35 mm to 90 mm in comparison to approximately 40 mm to 64 mm for a known lens. A lower circle of confusion and corresponding extended depth of field may also be achieved by implementing a sensor with higher resolution such as a 4K sensor, a 8K sensor or the like.

Figure 10:
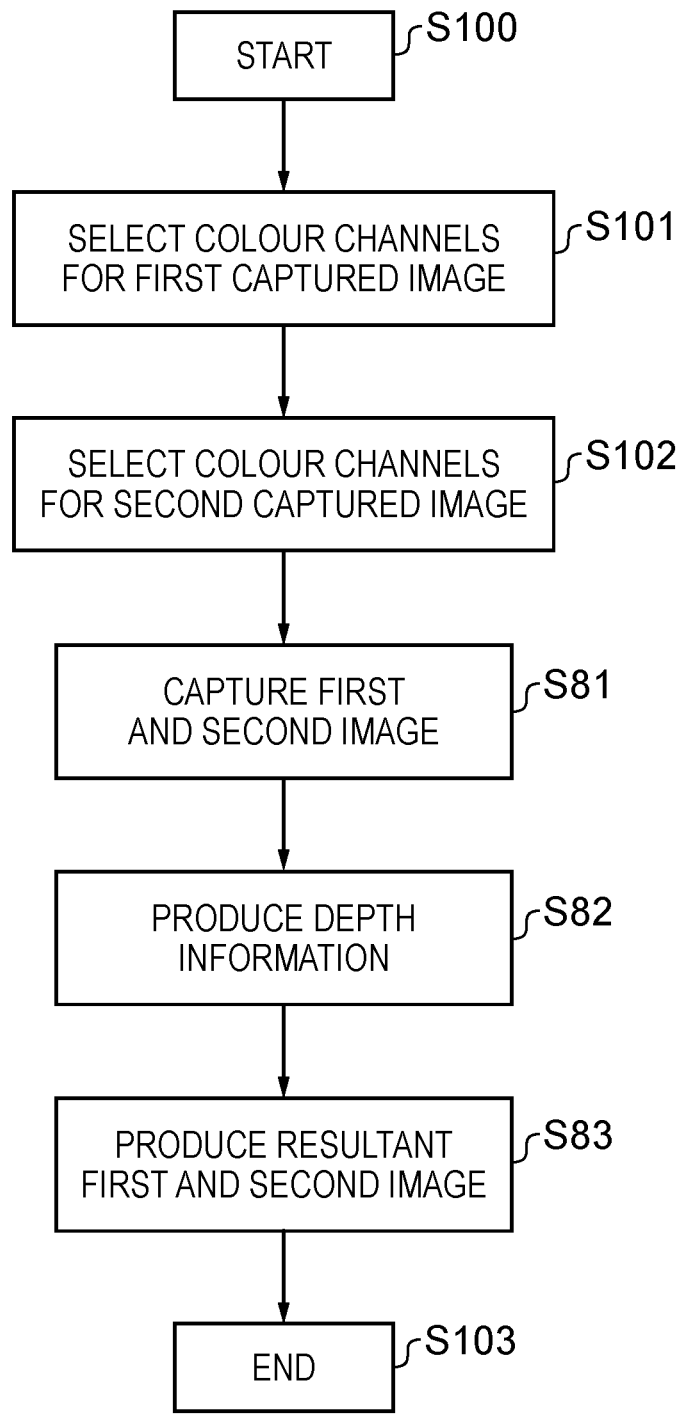
FIG. 10 shows a flow chart for the processing steps performed by the image sensor circuitry 404 and the processor circuitry 408 according to an embodiment of the disclosure.

FIG. 10 shows a flow chart for the processing steps performed by the image sensor circuitry 404 and the processor circuitry 408 according to an embodiment of the disclosure. Steps S101 to S81 are performed by the image sensor circuitry 404 and steps S82 and S83 are performed by the processor circuitry 408. Processing begins at step S100 and progresses to step S101. In step S101 the image sensor circuitry 404 selects colour channels for the first captured image. Said selected colour channels could comprise any number of wavelengths which the image sensor circuitry 404 is sensitive to, and could be fixed or set by some user operation. In step S102 the image sensor circuitry 404 selects colour channels for the second captured image. Said selected colour channels may typically be the same colour channels as selected for the first captured image, or may be a separate selection of colour channels. Step S81 performed by the image sensor circuitry 404 and steps S82 and S83 performed by the processor circuitry 408 are the same as those described for FIG. 8; as such a repetition of the description of these steps shall not be included for brevity. Processing ends with step 103.

Figure 11:
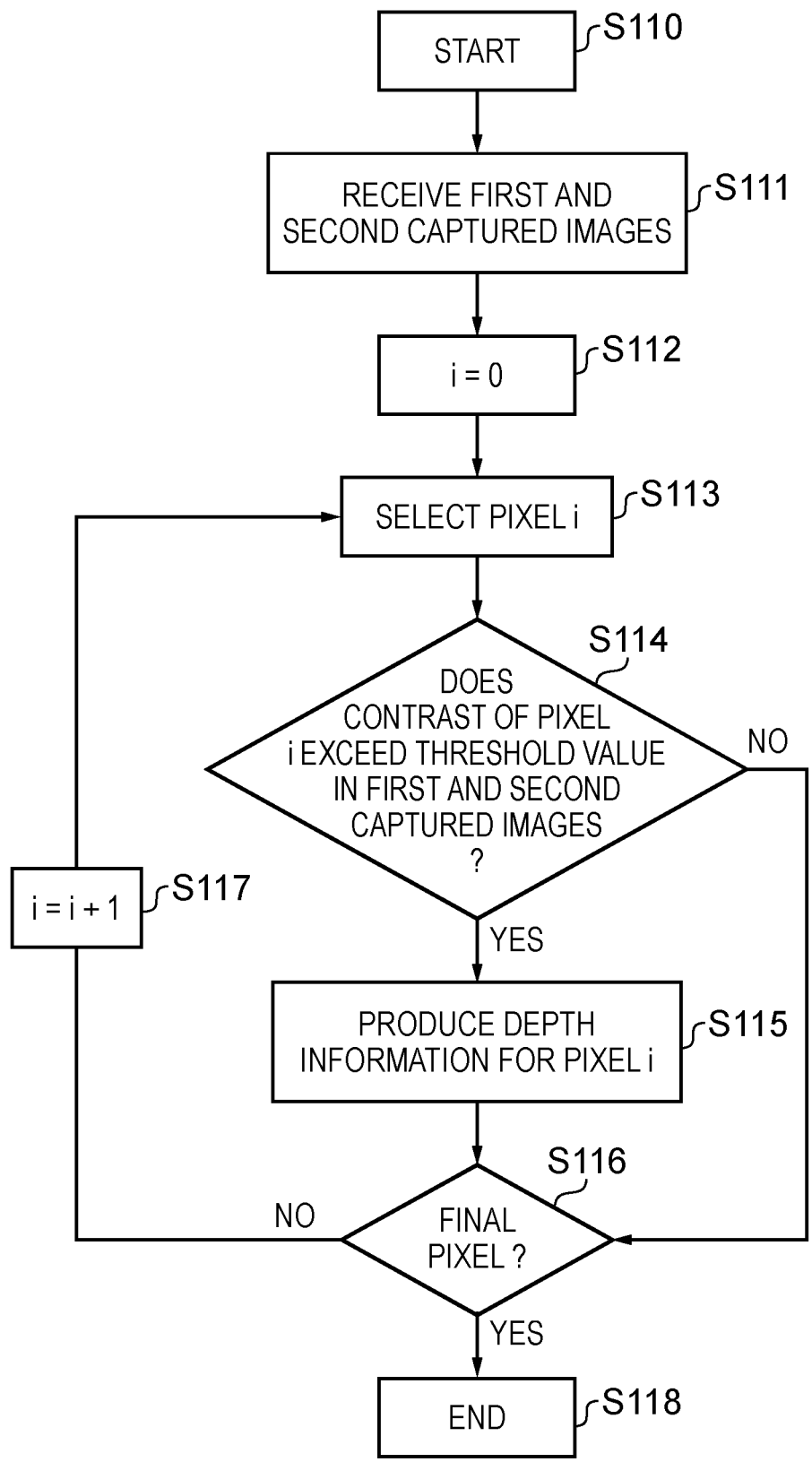
FIG. 11 depicts a flow chart describing the processing steps taken by the processor circuitry 408 to obtain the depth information of the scene according to an embodiment of the disclosure.

FIG. 11 depicts a flow chart describing the processing steps taken by the processor circuitry 408 to obtain the depth information of the scene according to an embodiment of the disclosure. Processing begins at step S110 and moves on to step S111. At step S111, the processor circuitry 408 is configured to receive the first and second captured images from the image sensor circuitry 404. At step S112 the processor circuitry 408 sets a value i=0. In step S113 the processor circuitry 408 then selects the pixel i corresponding to the first pixel in the first and second captured images. According to this embodiment of the disclosure, the processor circuitry 408 determines whether the contrast of pixel i exceeds a threshold value in the first and second captured images in step S114. If pixel i exceeds the threshold value then the processing moves to step S115, and the processor circuitry 408 produces depth information relating to pixel i (using any method described above for step S82 of FIG. 8) and processing continues to step S116. It will be understood that the value of the threshold may be set depending on the context of the application. Furthermore, the processor circuitry 408 may be configured to perform an alternative test on the pixel in step S114 to determine the suitability for producing depth information for a given pixel. If it is determined that pixel i fails to exceed the threshold value in step S114 then no depth information will be produced relating to pixel i and processing continues directly to step S116. If it is determined in step S112 that pixel i is the final pixel in the first and second image then processing continues to Step S116 and reaches the end of the process. However, if there are pixels remaining in the image which have not been processed then the processing moves to step S117 and the processor circuitry 408 increases the value i before selecting the next pixel in the first and second image in Step S113. As such, the depth information obtained by the processor circuitry 408 may have a resolution equal to or less than the resolution of the first and second image received in step S111 from the image sensor circuitry 404.

Figure 12:
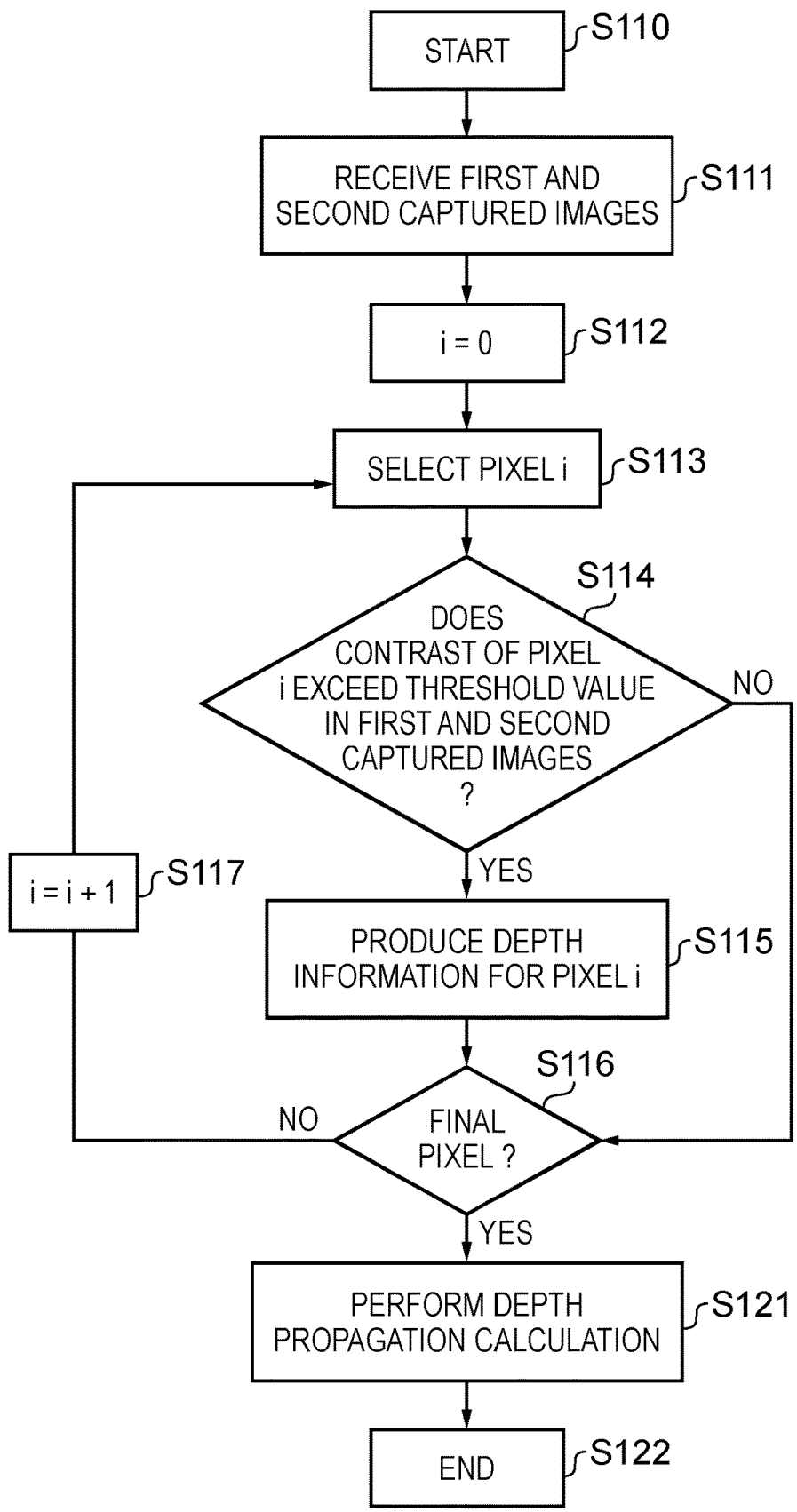
FIG. 12 shows a flow chart of the processing steps taken by processor circuitry 408 to obtain depth information of the scene according to an embodiment of the disclosure.

FIG. 12 shows a flow chart of the processing steps taken by processor circuitry 408 to obtain depth information of the scene according to an embodiment of the disclosure. Steps S111 to S117 are the same as those described in association with FIG. 11. According to this embodiment, the processor circuitry 408 may be further configured to perform additional step S121 once the all the pixels in the image have been processed. That is, at step S121 the processor circuitry has obtained depth information relating to the scene which may have a resolution equal to or less than the resolution of the first and second images received from the image sensor circuitry 404 in step S111. Then, in step S121 the processor circuitry performs a depth propagation calculation. That is, the processor circuitry 408 transports depth information from regions of the scene having depth information to regions of the scene which were determined in step S114 to be unsuitable for producing depth information. It will be understood that any suitable calculation known in the art may be used to perform the depth propagation calculation in step S121. As such, in step S121 the processor circuitry 408 produces depth information having the same resolution as the first and second images received in step S111 from the image sensor circuitry 404. It will be appreciated that the depth values may be used for many processes including metrology and 3D visualization in addition to the image visualization of the present embodiment.

Figure 13:
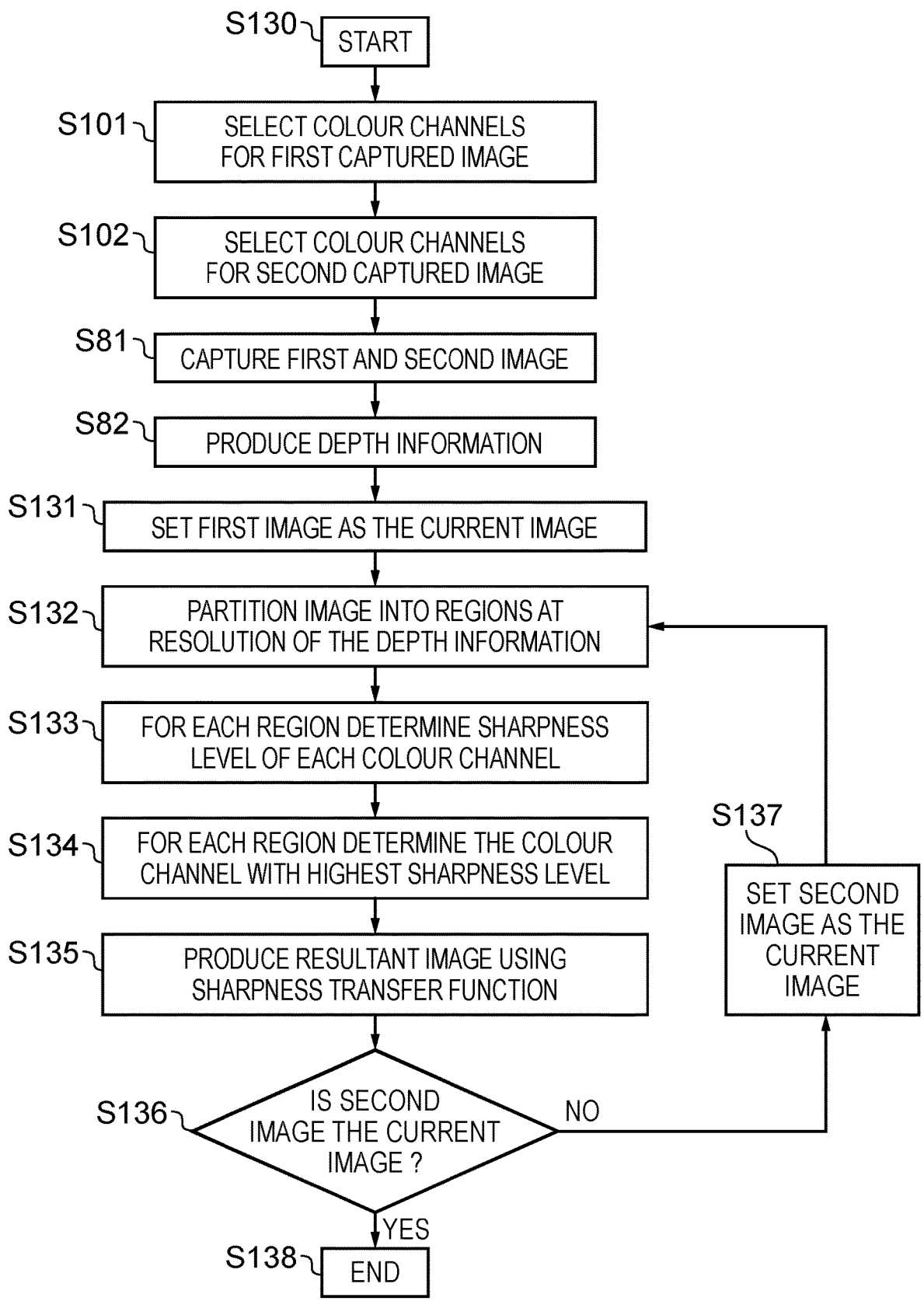
FIG. 13 is a depiction of the processing steps performed by the image sensor circuitry 404 and the processor circuitry 408 according to another embodiment of the disclosure.

FIG. 13 is a depiction of the processing steps performed by the image sensor circuitry 404 and the processor circuitry 408 according to an embodiment of the disclosure. Steps 101 to S81 are performed by the image sensor circuitry 404 while steps S82 to S136 are performed by the processor circuitry 408. Processing begins at step S130 and moves on to step S101. Steps S101 to S82 are the same as described in FIG. 9 so a repetition of the description of these steps will not be included for brevity. In step S131, the processor circuitry 408 designates the first captured image as the current image to be processed. In step S132 the processor circuitry partitions the current image into regions at the resolution of the depth information. That is, the processor circuitry partitions the image into regions whereby each region has depth information produced by processing step S82. In step S133 the processor circuitry determines the sharpness level of each colour channel of the current image. That is, the sharpest colour channel for each region of the image may be identified using depth information acquired from the stereoscopic image pair. The skilled person will appreciate that any appropriate method known in the art may be used to determine the sharpness level of each region in each colour channel. In processing step S134 the processor circuitry uses the measure of sharpness obtained in S133 to determine for each region of the image the colour channel with the highest sharpness level.

Furthermore, in processing step S135 the processor circuitry produces a resultant image of the scene using a sharpness transfer function to transfer image detail from the colour channel of each region having the highest sharpness level to the complementary colour channels in the corresponding regions of the image having a lower sharpness level. The sharpness transfer function enables the processor circuitry 408 to produce a reconstructed image having extended depth of field. It shall be understood that transporting the sharpness level from the colour channel having the highest sharpness level to the complementary colour channel for each region of the first and second image may be carried out using any suitable sharpness transport technique such as those known in the art.

In processing step S136 the processor circuitry 408 determines whether the current image is the first or second image captured by the image sensor circuitry 404. If the image is the first image then processing continues to step S137 where the second image is set as the current image and processing steps S132 to S136 are repeated for the second image. If however in step S136 it is determined that the current image is the second image, that is that the sharpness transfer function has been used to produce a resultant image for both the first and second image, then the processing will end with step S138.

Figure 14:
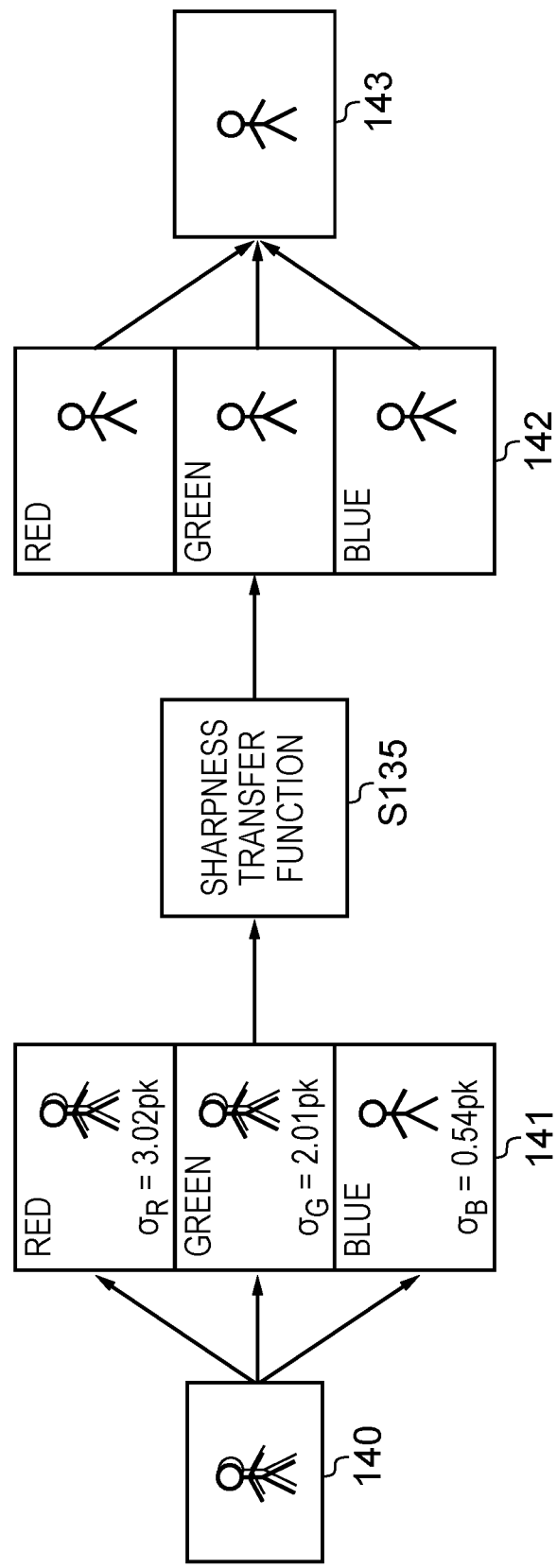
FIG. 14 depiction of the extended depth of field and sharpness transfer in accordance with embodiments of the disclosure.

FIG. 14 shows a depiction of the extended depth of field and sharpness transfer in accordance with embodiments of the disclosure. It shall be understood that this merely represents an effect of processing steps performed by processor circuitry 408 according to embodiments of the disclosure. Image 140 is received by the processor circuitry 408 and is separated into three colour channels 141. As described above, the plurality of colour channels is not limited to the number or the wavelengths shown in this example. Due to the hyperchromatic properties of lenses 402 of the medical imaging device 400, for a fixed object distance each colour channel will have a different sharpness level. In this example, the blue colour channel is determined as the colour channel having the highest sharpness of the three colour channels. That is, the sharpest colour channel for each region of the image may be identified using depth information acquired from the stereoscopic image pair. As described above, different colour channels have a higher sharpness level for different regions of the image. Step S135 is the same as that described for FIG. 13, and as such a repetition of the description shall not be included for brevity. Image 142 shows the resultant colour channels of Image 140 once the processor circuitry 408 has performed the sharpness transfer function in step S135. The sharpness level of the colour channel with the highest sharpness level in each region of image 140 has been transferred to the complementary colour channels. Image 143 is the resultant image produced by the processor circuitry 408 corresponding to image 140 and having an extended depth of field.

According to embodiments of the disclosure the tightly coupled use of hyperchromatic lenses 402 arranged in a stereoscopic configuration with the above digital processing techniques gives advantage of extended depth of field and higher resolution than known medical imaging devices.

Figure 15:
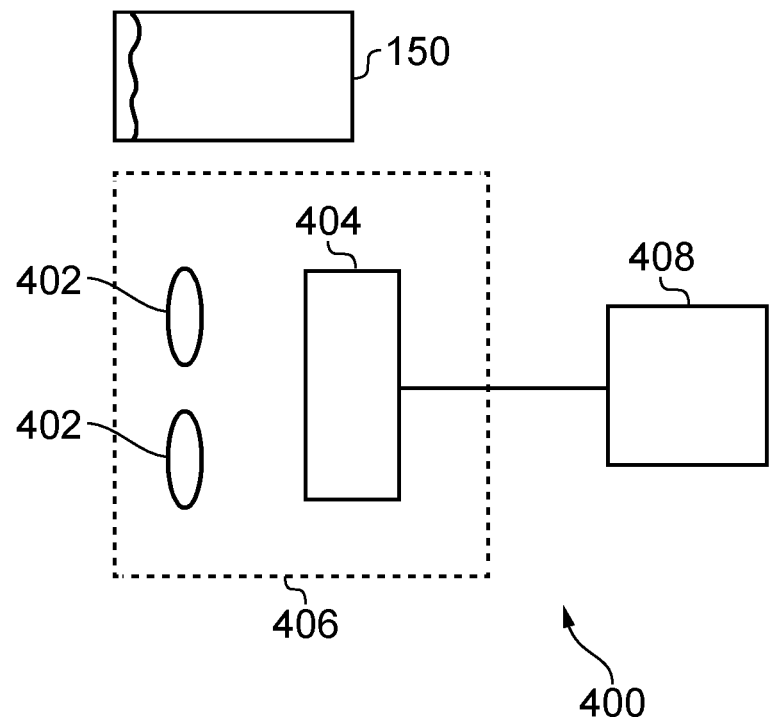
FIG. 15 is a schematic depiction of the medical imaging device according to an embodiment of the disclosure.

FIG. 15 is a schematic depiction of the medical imaging device according to an embodiment of the disclosure. Common elements of the device are numbered the same as in FIG. 4. In addition to these elements the medical imaging device comprises a light source 150. The light source 150 is configured such that it may illuminate the scene. The light source may be configured to produce broadband light comprising a plurality of wavelengths. Such a broadband light source may be a light emitting diode. The light source 150 may also be a narrow band light source such as a number of lasers. Illumination of the scene may be realized using fibre optical elements or any other suitable mechanism known in the art. As described above, a property of the hyperchromatic lenses 402 is the continuous change of focal length as a function of the wavelength of light applied. With narrow band illumination a discreet number of focal points can be generated. As such, use of narrow band illumination may further increase the level of sharpness transfer that can be achieved, since each individual captured colour channel may have a higher sharpness level as there will be less blur in each of the colour bands due to nearby wavelengths. Furthermore, use of narrow band illumination may reduce the complexity of digital image processing performed by processor circuitry 408 leading to a further reduction of size and cost of the medical imaging device 400 according to embodiments of the disclosure.

Figure 16:
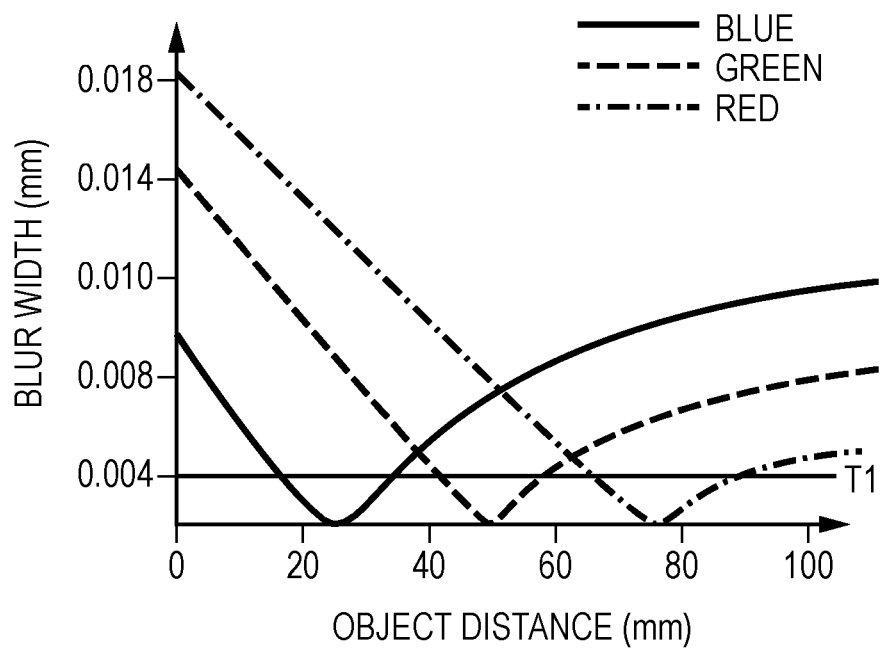
FIG. 16 shows a resultant graph of the blur width against wavelength for the optical portion 406 of the medical imaging device 400 of FIG. 4 when the scene is illuminated with narrow band light.

FIG. 16 shows a resultant graph of the blur width against wavelength for the optical portion 406 of the medical imaging device 400 of FIG. 4 when the scene is illuminated with narrow band light. As previously described, while the blur width is below the threshold level T1 it may be considered that there is an acceptable level of blur in the image. It will be appreciated that the threshold value could be set according to the context of the application and indeed any method for quantifying the level of blur within the image as known in the art may be used as appropriate. When a narrow band illumination is used there is less blur in each of the colour bands due to nearby wavelengths. That is, the minimum blur width practically achievable in a given colour band is reduced. As such the sharpness level obtained by the medical imaging device 400 is increased and a sharper image with extended depth of field may be obtained.

Figure 17:
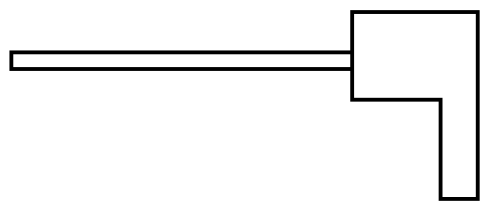
FIG. 17 is a schematic depiction of the medical imaging device according to embodiments of the disclosure where the medical imaging device is an endoscope.

FIG. 17 is a schematic depiction of the medical imaging device according to embodiments of the disclosure, wherein the medical imaging device is an endoscope.

Figure 18:
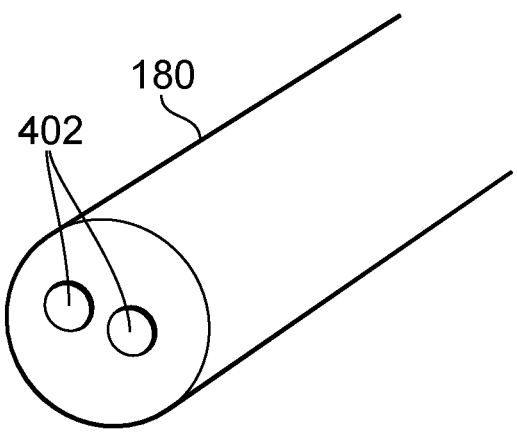
FIG. 18 is a schematic depiction of the medical imaging device according to embodiments of the disclosure wherein the medical imaging device is a chip-on-tip endoscope.

FIG. 18 is a schematic depiction of the medical imaging device according to embodiments of the disclosure wherein the medical imaging device is a chip-on-tip endoscope 180. Hyperchromatic lenses 402 are the same as those described in other embodiments of the disclosure and are arranged in a stereoscopic configuration such that depth information can be acquired for the sharpness transportation between colour channels as described above. The endoscope according to embodiments of the disclosure may be rigid or flexible. The endoscope tip may also include an illumination light source according to embodiments of the disclosure.

Figure 19:
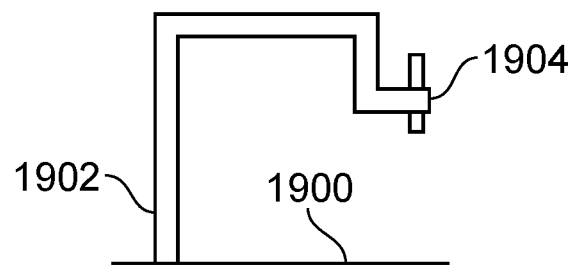
FIG. 19 is a medical imaging device according to embodiments of the disclosure wherein the medical imaging device is a surgical microscope.

FIG. 19 is a medical imaging device according to embodiments of the disclosure wherein the medical imaging device is a surgical microscope. The surgical microscope may comprise an arm 1902 and a base section 1900. The medical imaging device according to embodiments of the disclosure may be located in head section 1904, and may be used to provide high resolution image having an extended depth of field.

While embodiments of the disclosure have been described in relation to a medical imaging device, it will be appreciated that the claimed invention is not limited to medical imaging, and could be used in any imaging situation. The imaging device according to embodiments of the disclosure could be employed to effect in an industrial imaging device such as an industrial endoscopic device. For example, embodiments of the disclosure could be used in architectural endoscopy, whereby a scale version of a new building or complex can be correctly viewed from the perspective of a person walking through the architectural creation improving the visualisation, design and construction of proposed buildings.

Embodiments of the disclosure could be used for internal visualisation of works of engineering. For example, an imaging device according to embodiments of the disclosure could be used to view the interior of underground pipe systems, such as water pipes, in order to locate leaks or generally survey the structure. An imaging device according to embodiments of the disclosure could also be used for quality control and internal inspection of other mechanical systems such as turbines and engine components.

Alternatively, embodiments of the disclosure could be used in the security and surveillance industry. For example, an imaging device according to embodiments of the disclosure could be used to conduct surveillance in an area where the presence of a person is restricted, such as in an enclosed area or a very tight space.

In all these applications, an imaging device according to embodiments of the disclosure able to capture high resolution images with an extended depth of field would be advantageous. It will be appreciated that the above are merely examples of possible industrial applications of an imaging device according to embodiments of the disclosure, and many further applications of the imaging device are possible.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

Various embodiments of the present disclosure are defined by the following numbered clauses:

1) An imaging device for producing images of a scene, the imaging device comprising:
    a first and a second hyperchromatic lens being arranged in a stereoscopic configuration to receive light from the scene;
    image sensor circuitry configured to capture a first and second image of the light encountered by the first and the second lens respectively;
    processor circuitry configured to: produce depth information using the captured first and second images of the scene and produce a resultant first and second image of the scene using both the captured first and second image and the depth information.
2) The imaging device according to any clause, wherein the image sensor circuitry is configured to detect a first plurality of colour channels for the first captured image and a second plurality of colour channels for the second captured image.
3) The imaging device according to any clause, wherein the first and second plurality of colour channels can be selected from infrared, red, green, blue and ultraviolet.
4) The imaging device according to any clause, wherein the processor circuitry is configured to:
    partition the captured first and second images into regions corresponding to the resolution of the depth information;
    obtain for each region of the captured first and second images an image sharpness level for each colour channel using the depth information;
    determine for each region of the captured first and second image the colour channel having the highest sharpness level; and
    produce the resultant first and second image of the scene by transporting for each region of each of the captured first and second images the image sharpness level from the colour channel having the highest sharpness level to the corresponding region in the complementary colour channels for that image.
5) The imaging device according to any clause, wherein the processor circuitry is further configured to produce the depth information by comparing corresponding pixels between the captured first and second image where the contrast level of the pixels exceeds a given threshold value.
6) The imaging device according to any clause, wherein the processor circuitry is further configured to perform a depth information propagation calculation to produce depth information having a resolution corresponding to the resolution of the captured first and second images and wherein each region corresponds to a single pixel.
7) The imaging device according to any clause, wherein the resultant first and second image of the scene are images having an extended depth of field.
8) The imaging device according to any clause, further comprising a light source.
9) The imaging device according to any clause, wherein the light source is formed from at least one Light Emitting Diode or at least one Laser.
10) The imaging device according to any clause, wherein the image sensor circuitry comprises a 4K sensor.
11) The imaging device according to any clause, wherein the imaging device is an endoscope.
12) The imaging device according to any clause, wherein the imaging device is a medical imaging device.
13) The imaging device according any clause, wherein the imaging device is an industrial imaging device.
14) A method for producing images of a scene, the method comprising:
    receiving light from a scene using a first and a second hyperchromatic lens arranged in a stereoscopic configuration;
    capturing a first and second image of the light encountered by the first and second lens respectively;
    producing depth information using the captured first and second images of the scene; and
    producing a resultant first and second image of the scene using both the first and second image and the depth information.
15) A recording medium storing a computer program for controlling a computer to perform a method for producing images of a scene, the method comprising:
    receiving light from a scene using a first and a second hyperchromatic lens arranged in a stereoscopic configuration;
    capturing a first and second image of the light encountered by the first and second lens respectively;
    producing depth information using the captured first and second images of the scene; and
    producing a resultant first and second image of the scene using both the first and second image and the depth information.

The invention claimed is:

1. An imaging device for producing images of a scene, the imaging device comprising:
    a first and a second hyperchromatic lens being arranged in a stereoscopic configuration to receive light from the scene;
    image sensor circuitry configured to capture a first and second image of the light encountered by the first and the second lens respectively;
    processor circuitry configured to:
    produce depth information using the captured first and second images of the scene and produce a resultant first and second image of the scene using both the captured first and second image and the depth information;
    partition the captured first and second images into regions corresponding to a resolution of the depth information;
    obtain for each region of the captured first and second images an image sharpness level for each colour channel using the depth information;
    determine for each region of the captured first and second image the colour channel having the highest sharpness level;
    produce the resultant first and second image of the scene by transporting for each region of each of the captured first and second images the image sharpness level from the colour channel having the highest sharpness level to the corresponding region in the complementary colour channels for that image; and
    perform a depth information propagation calculation to produce depth information having a resolution corresponding to the resolution of the captured first and second images and wherein each region corresponds to a single pixel.

2. The imaging device according to claim 1, wherein the image sensor circuitry is configured to detect a first plurality of colour channels for the first captured image and a second plurality of colour channels for the second captured image.

3. The imaging device according to claim 2, wherein the first and second plurality of colour channels can be selected from infrared, red, green, blue and ultraviolet.

4. The imaging device according to claim 1, wherein the processor circuitry is further configured to produce the depth information by comparing corresponding pixels between the captured first and second image where the contrast level of the pixels exceeds a given threshold value.

5. The imaging device according to claim 1, wherein the resultant first and second image of the scene are images having an extended depth of field.

6. The imaging device according to claim 1, further comprising a light source.

7. The imaging device according to claim 6, wherein the light source is formed from at least one Light Emitting Diode or at least one Laser.

8. The imaging device according to claim 1, wherein the image sensor circuitry comprises a 4K sensor.

9. The imaging device according to claim 1, wherein the imaging device is an endoscope.

10. The imaging device according to claim 1, wherein the imaging device is a medical imaging device.

11. The imaging device according claim 1, wherein the imaging device is an industrial imaging device.

12. A method for producing images of a scene, the method comprising:
receiving light from a scene using a first and a second hyperchromatic lens arranged in a stereoscopic configuration;
capturing a first and second image of the light encountered by the first and second lens respectively;
producing depth information using the captured first and second images of the scene;
producing a resultant first and second image of the scene using both the first and second image and the depth information;
partitioning the captured first and second images into regions corresponding to a resolution of the depth information;
obtaining for each region of the captured first and second images an image sharpness level for each colour channel using the depth information;
determining for each region of the captured first and second image the colour channel having the highest sharpness level;
producing the resultant first and second image of the scene by transporting for each region of each of the captured first and second images the image sharpness level from the colour channel having the highest sharpness level to the corresponding region in the complementary colour channels for that image; and
performing a depth information propagation calculation to produce depth information having a resolution corresponding to the resolution of the captured first and second images and wherein each region corresponds to a single pixel.

13. The method according to claim 12, further comprising producing the depth information by comparing corresponding pixels between the captured first and second image where a contrast level of the pixels exceeds a given threshold value.

14. A non-transitory recording medium storing a computer program for controlling a computer to perform a method for producing images of a scene, the method comprising:
receiving light from a scene using a first and a second hyperchromatic lens arranged in a stereoscopic configuration;
capturing a first and second image of the light encountered by the first and second lens respectively;
producing depth information using the captured first and second images of the scene;
producing a resultant first and second image of the scene using both the first and second image and the depth information;
partitioning the captured first and second images into regions corresponding to a resolution of the depth information;
obtaining for each region of the captured first and second images an image sharpness level for each colour channel using the depth information;
determining for each region of the captured first and second image the colour channel having the highest sharpness level;
producing the resultant first and second image of the scene by transporting for each region of each of the captured first and second images the image sharpness level from the colour channel having the highest sharpness level to the corresponding region in the complementary colour channels for that image; and
performing a depth information propagation calculation to produce depth information having a resolution corresponding to the resolution of the captured first and second images and wherein each region corresponds to a single pixel.

15. The non-transitory recording medium according to claim 14, wherein the method further comprises producing the depth information by comparing corresponding pixels between the captured first and second image where a contrast level of the pixels exceeds a given threshold value.

* * * * *